(12) United States Patent
Vukovic

(10) Patent No.: US 9,719,970 B2
(45) Date of Patent: Aug. 1, 2017

(54) METHODS AND APPARATUS FOR THE ANALYSIS OF VITAMIN D METABOLITES

(71) Applicant: Waters Technologies Corporation, Milford, MA (US)

(72) Inventor: John Vukovic, Mississauga (CA)

(73) Assignee: Waters Technologies Corporation, Milford, MA (US)

(*) Notice: Subject to any disclaimer, the term of this patent is extended or adjusted under 35 U.S.C. 154(b) by 116 days.

(21) Appl. No.: 14/648,197

(22) PCT Filed: Nov. 26, 2013

(86) PCT No.: PCT/US2013/072057
§ 371 (c)(1),
(2) Date: May 28, 2015

(87) PCT Pub. No.: WO2014/085486
PCT Pub. Date: Jun. 5, 2014

(65) Prior Publication Data
US 2015/0308987 A1    Oct. 29, 2015

Related U.S. Application Data

(60) Provisional application No. 61/731,883, filed on Nov. 30, 2012.

(51) Int. Cl.
*G01N 30/34* (2006.01)
*G01N 30/02* (2006.01)
(Continued)

(52) U.S. Cl.
CPC ............. *G01N 30/34* (2013.01); *G01N 30/02* (2013.01); *G01N 30/88* (2013.01); *G01N 33/82* (2013.01);
(Continued)

(58) Field of Classification Search
CPC ........... G01N 2030/8813; G01N 30/34; G01N 30/88; G01N 33/82; G01N 33/538;
(Continued)

(56) References Cited

U.S. PATENT DOCUMENTS 4,500,432 A    2/1985    Poole et al.
5,792,331 A    8/1998    Srinivasan et al.
(Continued)

FOREIGN PATENT DOCUMENTS

AU    640010 B2    8/1993
CA    1327476 C    3/1994
(Continued)

OTHER PUBLICATIONS

Aubin, A. "Analysis of fat-soluble vitamin capsules using ultraperformance convergence chromatography (UPC2)". Jun. 2012. http://www.waters.com/webassets/cms/library/docs/720004394en.pdf.*

(Continued)

*Primary Examiner* — Jennifer Wecker
(74) *Attorney, Agent, or Firm* — McCarter & English, LLP; Deborah M. Vernon

(57) ABSTRACT

The present disclosure relates to $CO_2$-based chromatography for the efficient and precise separation of Vitamin D metabolites.

11 Claims, 3 Drawing Sheets

(51) Int. Cl.

| | | |
|---|---|---|
| *G01N 1/18* | (2006.01) | |
| *G01N 33/82* | (2006.01) | |
| *G01N 30/88* | (2006.01) | |
| *B01D 15/40* | (2006.01) | |
| *B01D 11/02* | (2006.01) | |
| *H01J 49/00* | (2006.01) | |
| *G01N 30/72* | (2006.01) | |
| *G01N 33/68* | (2006.01) | |
| *G01N 33/538* | (2006.01) | |

(52) U.S. Cl.
CPC .......... *B01D 11/0203* (2013.01); *B01D 15/40* (2013.01); *C12N 2500/38* (2013.01); *G01N 30/72* (2013.01); *G01N 30/7233* (2013.01); *G01N 33/538* (2013.01); *G01N 33/6848* (2013.01); *G01N 2030/027* (2013.01); *G01N 2030/8813* (2013.01); *H01J 49/0027* (2013.01)

(58) Field of Classification Search
CPC .... G01N 30/02; G01N 30/72; G01N 33/6848; G01N 2030/027; B01D 15/40; C12N 2500/38
See application file for complete search history.

(56) References Cited

U.S. PATENT DOCUMENTS

| | | | |
|---|---|---|---|
| 6,074,541 A | 6/2000 | Srinivasan et al. | |
| 6,656,358 B2 | 12/2003 | May et al. | |
| 6,982,142 B2 | 1/2006 | Cabot | |
| 7,207,967 B1 | 4/2007 | Bellhouse et al. | |
| 7,763,292 B2 | 7/2010 | Gutierrez-Uribe et al. | |
| 7,972,867 B2 | 7/2011 | Clarke et al. | |
| 8,088,795 B2 | 1/2012 | Lacrampe et al. | |
| 8,133,694 B2 * | 3/2012 | Armbruster | G01N 33/82 435/7.1 |
| 8,168,644 B2 | 5/2012 | Freyne et al. | |
| 8,173,442 B2 | 5/2012 | Holmquist et al. | |
| 8,232,298 B2 | 7/2012 | Lacrampe et al. | |
| 8,288,377 B2 | 10/2012 | Storck et al. | |
| 8,299,256 B2 | 10/2012 | Vialard et al. | |
| 2001/0001801 A1 * | 5/2001 | Johannsen | C07C 401/00 552/500 |
| 2002/0139752 A1 * | 10/2002 | Berger | B01D 11/0203 210/656 |
| 2002/0182260 A1 | 12/2002 | Mak et al. | |
| 2004/0043089 A1 | 3/2004 | Rabie | |
| 2005/0037386 A1 | 2/2005 | Morrison et al. | |
| 2006/0188397 A1 * | 8/2006 | Chordia | G01N 30/82 422/70 |
| 2006/0228809 A1 * | 10/2006 | Clarke | G01N 33/82 436/173 |
| 2009/0137056 A1 * | 5/2009 | Holmquist | G01N 33/82 436/127 |
| 2010/0024637 A1 | 2/2010 | Jang | |
| 2010/0178368 A1 | 7/2010 | Kreuter | |
| 2010/0216729 A1 | 8/2010 | Gutierrez-Uribe et al. | |
| 2010/0222348 A1 | 9/2010 | Angibaud et al. | |
| 2010/0236137 A1 | 9/2010 | Wu et al. | |
| 2011/0130418 A1 | 6/2011 | Poncelet et al. | |
| 2011/0195513 A1 * | 8/2011 | Calton | G01N 30/14 436/131 |
| 2011/0263622 A1 | 10/2011 | Angibaud et al. | |
| 2011/0294846 A1 | 12/2011 | Schoentjes et al. | |
| 2012/0053242 A1 | 3/2012 | Cela Lopez | |
| 2012/0071508 A1 | 3/2012 | Lacrampe et al. | |
| 2013/0126721 A1 * | 5/2013 | Carlton | G01N 33/82 250/282 |
| 2014/0047906 A1 * | 2/2014 | Herman | G01N 30/7233 73/61.55 |
| 2014/0319057 A1 * | 10/2014 | Brousmiche | B01D 15/26 210/656 |

FOREIGN PATENT DOCUMENTS

| | | |
|---|---|---|
| CA | 2079890 C | 12/1996 |
| CA | 1339498 C | 10/1997 |
| CA | 2720686 A1 | 10/2009 |
| CA | 2770245 A1 | 2/2011 |
| CN | 1220497 C | 9/2005 |
| CN | 100347156 C | 11/2007 |
| CN | 102558006 A | 7/2012 |
| WO | 98/52428 A2 | 11/1998 |
| WO | 2005/039381 A2 | 5/2005 |
| WO | 2008/050821 A1 | 5/2008 |
| WO | 2008/136428 A1 | 11/2008 |
| WO | 2011/014122 A1 | 2/2011 |
| WO | 2011/135376 A1 | 11/2011 |
| WO | 2012/016706 A1 | 2/2012 |

OTHER PUBLICATIONS

Aurand, C.R. et al. Fast and accurate LC-MS analysis of vitamin D metabolites using Ascentis express f5 hplc columns. Reporter, vol. 29.2, pp. 3-4 (2011 ).*

Aubin, A. Analysis of fat-soluble vitamin capsules using ultraperformance convergence chromatography (UPC2). Jun. 2012. http://www.waters.com/webassets/cms/library/docs/720004394en.pdf, last accessed Mar. 1, 2014.

Aubin, A.J. et al. Analysis of fat soluble vitamin capsules using ultraperformance convergence chromatography. AOAC International Meeting, Oct. 2, 2012. https://www.waters.com/webassets/cms/library/docs/2012other_burgess_fat_soluble_vitamin_capsule.pdf, last accessed Feb. 26, 2014.

Aurand, C.R. et al. Fast and accurate LC-MS analysis of vitamin D metabolites using Ascentis express f5 hplc columns. Reporter, vol. 29.2, pp. 3-4 (2011).

Beaulieu, N. et al. Liquid-chromatographic methods for vitamins A and D in multivitamin-mineral formulations. J. Assoc. Off. Anal. Chem. 72(2), 247-254 (1989).

Board, R. et al. The use of modifiers in supercritical fluid chromatography with carbon dioxide. ChemSA 12, 21-2, 24 CEDEN: CHEMDU (Jun. 1983) Abstract Only.

Brunner, G. et al. New aspects on adsorption from supercritical fluid phases. J Supercritical Fluids, vol. 38, No. 2, pp. 181-200 (Sep. 2006).

Burri, B. et al. Supercritical fluid extraction and reversed-phase liquid chromatography methods for vitamin A and ?-carotene Heterogeneous distribution of vitamin A in the liver. Journal of Chromatography A, vol. 762, No. 1-2, pp. 201-206 (Feb. 1997).

Buss, V. Preparative-scale chromatography with supercritical fluids for vitamin purification. Dissertation. Fortschritt-Berichte VDI, Reihe 3: Verfahrenstechnik(778), 131 Reference(s), I-XIII, 1-138, 56f, 30t (2003). German. Abstract Only.

Calton, L.J. Measurement of 25-hydroxyvitamin D3 and C3-epi-25-hydroxyvitamin D3 using UPLC/MS/MS in pediatric and adult populations. 2011. Downloaded from http://www.waters.com/posters.

Ibanez, E. et al. Optimization of Fat-Soluble Vitamin Separation by Supercritical Fluid Chromatography. Chromatographia vol. 40, No. 7/8: 448-452 (Apr. 1995).

Ibanez, E. et al. Optimization of Separation of Fat-Soluble Vitamins by Supercritical Fluid Chromatography Using Serial Micropacked Columns. J Agric Food Chem 43: 2667-2671 (1995).

International Search Report and Written Opinion issued in International Application No. PCT/US2013/72057, mailed Mar. 25, 2014.

Jarvis, M. Measurement of 25-OH-Vitamin D3 and 3-Epi-25_OH-Vitamin D3 by LC/MS/MS. AB SCIEX Publication No. 5250112-01 (2012).

Kamao, M. C-3 Epimerization of Vitamin D3 Metabolites and Further Metabolism of C-3 Epimers. J Biol Chem vol. 279, No. 16, pp. 15897-15907 (2004).

Lensmeyer, G. The C-3 Epimer of 25-Hydroxyvitamin D3 Is Present in Adult Serum. J Clin Endocrinol Metab, 97(1): 163-168 (Jan. 2012).

(56) References Cited

OTHER PUBLICATIONS

Manninen, P. et al. Method for Characterization of Triacylglycerols and Fat-Soluble Vitamins in Edible Oils and Fats by Supercritical Fluid Chromatography. JAOCS vol. 72, No. 9 (1995).

Matsumoto, K. et al. Development of directly coupled supercritical fluid chromatography with packed capillary column-mass spectrometry with atmospheric pressure chemical ionization. J Chromatography, 605(1), 87-94 (1992).

Matsumoto, K. et al. Fundamental Conditions in Pressure-Programmed Supercritical Fluid Chromatography-Mass Spectrometry and some Applications to Vitamin Analysis. Chromatographia vol. 21, No. 11: 617-621 (Nov. 1986).

Pyo, D. et al. Development of new analytical method of vitamins using supercritical fluid. Analytical Science & Technology 10(2): 131-138 (1997). Korean. Abstract Only.

Pyo, D. Separation of vitamins by supercritical fluid chromatography with water-modified carbon dioxide as the mobile phase. J Biochem Biophys Methods 43: 113-123 (2000).

Schleicher, R.L. Isotope dilution ultra performance liquid chromatography-tandem mass spectrometry method for simultaneous measurement of 25-hydroxyvitamin D2, 25-hydroxyvitamin D3 and 3-epi-25-hydroxyvitamin D3 in human serum. Clinica Chimica Acta 412: 1594-1599 (2011).

Schlingmann, K.P. Mutations in CYP24A1 and Idiopathic Infantile Hypercalcemia. N Engl J Med 365: 410-421 (2010).

Shen, Y. et al. Packed Capillary Column Supercritical Fluid Chromatography of Fat-soluble Vitamins Using Liquid Crystal Polysiloxane Coated Particles. Chromatographia vol. 43, No. 1/2: 53-58 (Jul. 1996).

Staby, A. et al. Quantitative Analysis of Marine Oils by Capillary Supercritical Fluid Chromatography. Chromatographia vol. 39, No. 11/12: 697-705 ( Dec. 1994).

Strathmann, F. G. 3-epi-25 hydroxyvitamin D concentrations are not correlated with age in a cohort of infants and adults. Clinica Chimica Acta 413: 203-206 (2012).

Turner, C. et al. Supercritical fluid extraction and chromatography for fat-soluble vitamin analysis. J Chromatography A, 936: 215-237 (2001).

Van Den Ouweland, J.M.W. et al. Fast Separation of 25-Hydroxyvitamin d3 from 3-epi-25-hydroxyvitamin d3 in human serum by liquid chromatography-tandem mass spectrometry: variable prevalence of 3-epi-25-hydroxyvitamin D3 in infants, children, and adults. Clin Chem vol. 57, pp. 1618-1619 (2011).

Van Den Ouweland, J.M.W. et al. Fast separation of 25-hydroxyvitamin D3 from its C3-epimer in human serum by liquid chromatography-tandem mass spectrometry showing variable C3-epimer prevalence in infants and adults. Ned Tijdschr Klin Chem Labgeneesk, vol. 37, pp. 227-229 (Jul. 2012).

Wang, H. et al. Chemical constituents of supercritical $CO_2$ extract from Valeriana jatamansi. Beijing Zhongyiyao Daxue Xuebao 30(12): 832-835, 853 (2007). Chinese. Abstract Only.

White, C.M. et al. Analysis of Pharmaceuticals and Other Solutes of Biochemical Importance by Supercritical Fluid Chromatography. J High Resolution Chromatography vol. 11:94-98 (Jan. 1988).

\* cited by examiner

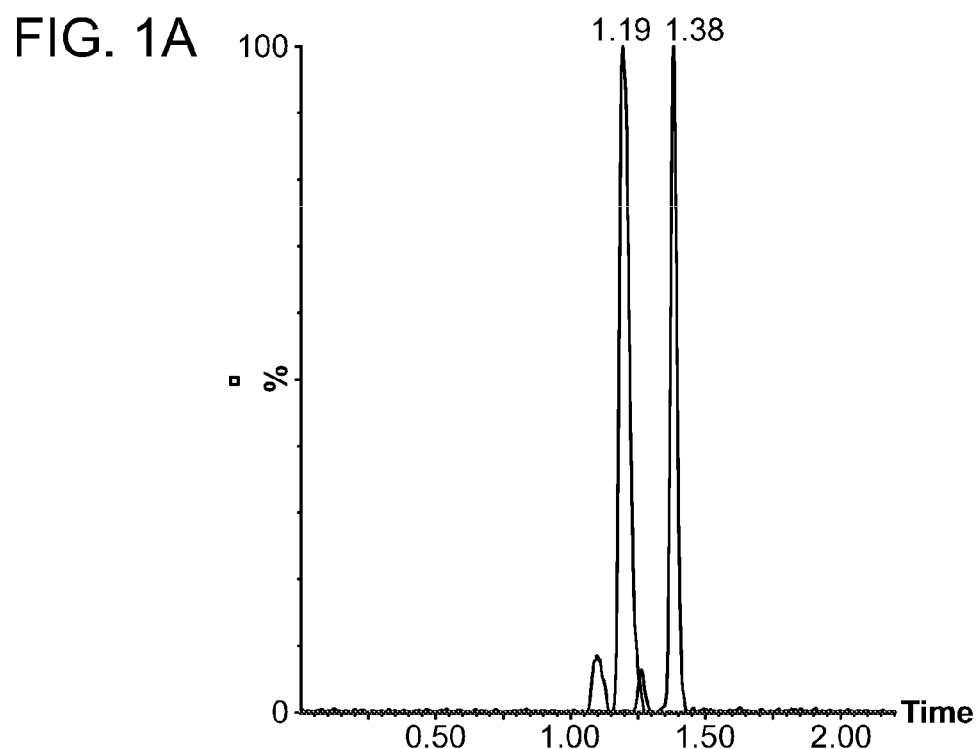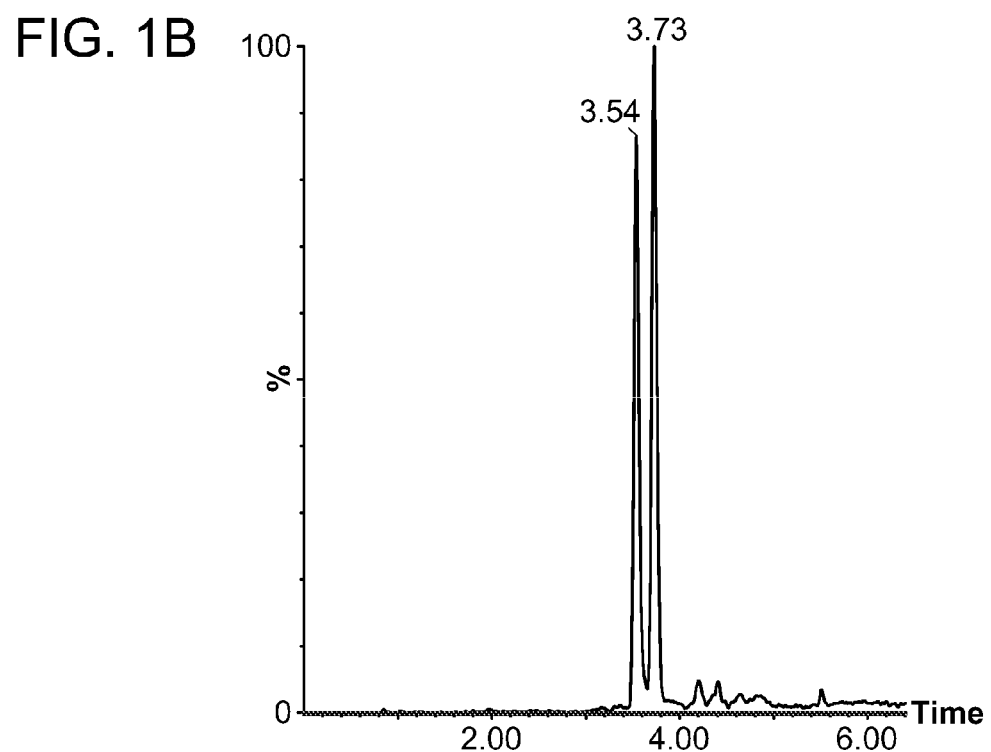

FIG. 2
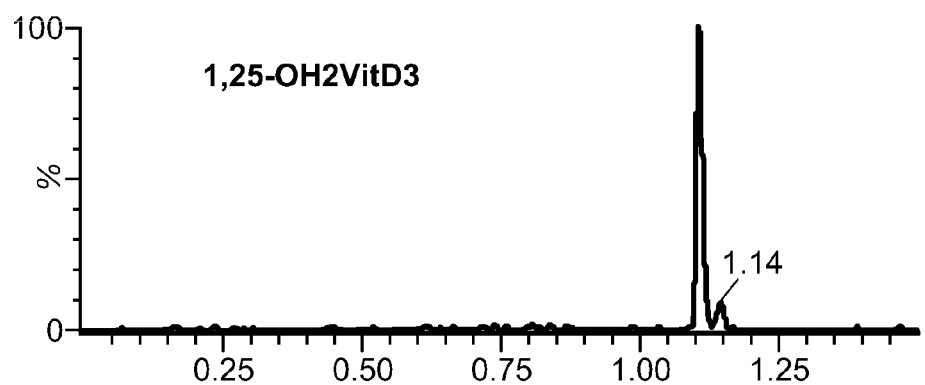
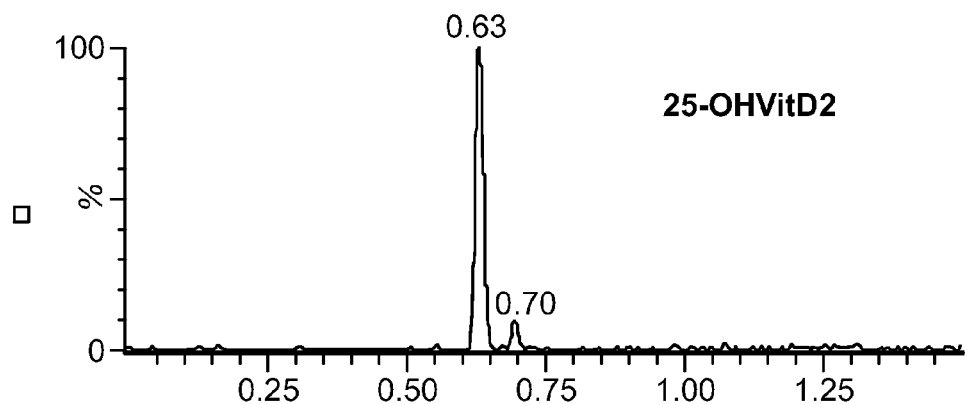
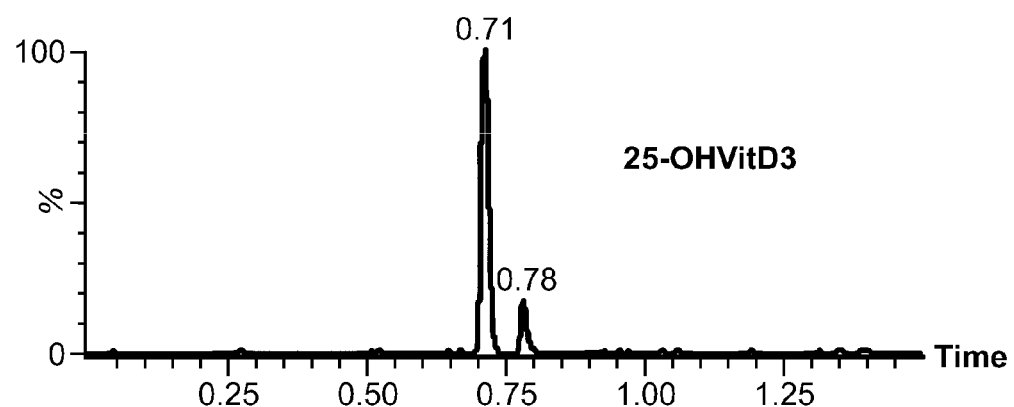

METHODS AND APPARATUS FOR THE ANALYSIS OF VITAMIN D METABOLITES

CROSS-REFERENCE TO RELATED APPLICATIONS

This application is a National Stage Application of International Application No. PCT/US2013/072057, filed Nov. 26, 2013, which claims priority to U.S. Provisional Application No. 61/731,883, filed Nov. 30, 2012, which Each of the foregoing applications is incorporated herein by reference in its entirety.

FIELD OF THE TECHNOLOGY

The present disclosure relates to $CO_2$-based chromatography for use in the analysis and characterization of Vitamin D metabolites.

BACKGROUND

Vitamin D is a fat-soluble secosteroid that is responsible for intestinal absorption of calcium and phosphate. The metabolic pathway for Vitamin D is complex and involves multiple mono-, di- and tri-hydroxy-forms of both Vitamin $D_3$ and Vitamin $D_2$ together with a number of epimer and "pre" isomers. In humans, Vitamin $D_3$ is synthesized in the skin by the action of sun-light while a relatively small amount of vitamin $D_2$ is obtained from dietary sources. In some cases, pharmaceutical Vitamin $D_2$ might be taken as a supplement. In the liver, Vitamin D is converted to 25-hydroxyvitamin D (abbreviated 25-OH-Vit-D) and current clinical practice uses the total serum 25-OH-Vit-D (i.e., 25-OH-Vit-$D_3$ plus 25-OH-Vit-$D_2$) levels to assess a person's Vitamin D status. The 25-OH-Vit-D metabolite is then converted primarily in the kidneys to the hormonally active form 1,25-dihydroxyvitamin D (abbreviated 1,25-$(OH)_2$-Vit-D). 1,25-$(OH)_2$-Vit-D circulates as a hormone in the blood and is responsible for regulating the concentration of calcium and phosphate in the bloodstream to promote healthy growth and remodeling of bone. 25-OH-Vit-D is also converted to 1,25-$(OH)_2$-Vit-D outside of the kidneys for other purposes, such as in the proliferation, differentiation, and apoptosis of cells.

Other metabolites also prove to be informative and relevant to the overall biological effect of Vitamin D. For example, while the metabolite 24,25-$(OH)_2$-Vit-D alone has no known biological activity, it represents the first step in the pathway to degrade 25-OH-Vit-D and is not routinely measured. The enzyme responsible (Vitamin D 24-hydroxylase; CYP24A1) plays an important role in maintaining a normal ("sufficient") concentration of 25-OH-Vit-D. Too high a concentration of 25-OH-Vit-D can cause hypercalcemia and recent evidence suggests that at least some cases of Idiopathic Infantile Hypercalcemia (IIH) might be the result of natural polymorphisms in the CYP24A1 gene.

It has been recently recognized that a structural isomer of 25-OH-Vit-$D_3$ (the C3-epimer), which was thought only to be present in pediatric samples, is also present in adults. C3-epi-25-OH-Vit-$D_3$ has no known biological relevance and it should therefore not be included in the measurement of Vitamin D status. Recent studies have highlighted that the majority of LC/MS/MS assays used by laboratories to report results to the Vitamin D External Quality Assurance Scheme (DEQAS) are not designed to differentiate between 25-OH-Vit-$D_3$ and the C3-epimer. This is because the two isomers (25-OH-Vit-$D_3$ and the C3-epimer) have identical chemical composition, molecular mass and MS/MS characteristics such that they cannot be separated solely on the basis of mass spectrometry. Instead, both isomers must first be separated from each other before they are introduced into the analyser region of the mass spectrometer. This can be achieved using conventional liquid chromatography. However, this difficult separation can take, if at all, from approximately 6 minutes to approximately 12 minutes per sample, which makes routine adoption of LC/MS based assays in a clinical laboratory impractical. Although some immunoassays are able to differentiate between 25-OH-Vit-$D_3$ and the C3-epimer, there are other interferences and difficulties which result in most immunoassays having relatively poor assay characteristics (accuracy, precision, linearity etc.). Thus, at present there appears to be no single assay for Vitamin D status that provides all the desirable assay characteristics.

LC/MS analyses can quantitatively measure multiple analytes in the same analytical run. For example, in addition to analyzing 25-OH-Vit-$D_2$ and 25-OH-Vit-$D_3$ separately from C3-epi-25-OH-Vit-$D_3$, an LC/MS method can also measure other Vitamin D metabolites (e.g., 24,25-$(OH)_2$-Vit-D, 1,25-$(OH)_2$-Vit-D, etc.) in the same analysis. Such a multi-analyte analysis can provide a much more robust Vitamin D status. However, the analysis times of an LC/MS Vitamin D metabolite panel such as this becomes lengthy and impractical for routine laboratories.

In addition, because some Vitamin D metabolites are present at low concentrations in serum and plasma (e.g., 1,25-$(OH)_2$-Vit-D, 1,24,25-$(OH)_3$-Vit-D, etc), derivatization methods with Cookson-type reagents (e.g., 4-phenyl-1,2,4-triazoline-3,5-dione (PTAD) and DMEQ-TAD (4-[2-(3,4-Dihydro-6,7-dimethoxy-4-methyl-3-oxo-2-quinoxalinyl) ethyl]-3H-1,2,4-triazole-3,5(4H)-dione)) to form, e.g., PTAD-linked Vitamin D metabolites derivatives, have been used as a way to increase the sensitivity of detecting these metabolites by mass spectrometry. However, this derivatization process results in pairs of isomeric derivatives for each analyte and may create inferences. Therefore, a significant challenge has been to resolve, in a short analysis time compatible with high sample throughput, these low concentration derivatives under current chromatographic techniques.

SUMMARY

Given the importance to accurately determine a person's Vitamin D status, and to further understand the biological implications involved in the metabolic pathway for Vitamin D, e.g., being able to effectively monitor a panel of Vitamin D metabolites to diagnosis conditions at an early stage, there is a need to develop efficient chromatographic methods for the precise analysis of Vitamin D metabolites. For example, an efficient and precise method of analyzing Vitamin D metabolites, such as analyzing 25-OH-Vit-$D_2$ and 25-OH-Vit-$D_3$ separately from C3-epi-25-OH-Vit-$D_3$, would prove useful in providing accurate measurements of a person's Vitamin D status. Also, increasing the separation efficiency of low concentration metabolites (e.g., 1,25-$(OH)_2$-Vit-D or 1,24,25-$(OH)_3$-Vit-D) and/or derivatives thereof provides a superior advancement in the commercial analysis of Vitamin D metabolite panels.

Exemplary embodiments of the present disclosure are directed to rapid and efficient methods for the separation of Vitamin D metabolites. The present disclosure is based, in part, on the discovery that a $CO_2$-based chromatography system (e.g., ACQUITY UPC2®, Waters Corporation, Milford, Mass.) with features, such as, e.g., improved pressure stability, improved sample injection, and superior column chemistry, could reproducibly substantially resolve metabolites of Vitamin D.

Many clinical laboratories have developed routine LC/MS/MS assays to assess Vitamin D status (i.e., the total concentration of 25-OH-Vit-D in serum) to replace automated immunoassay techniques that can suffer from interference. However, commercially efficient and effective separations of certain Vitamin D metabolites, particularly C3-epi-25-OH-Vit-$D_3$, has not yet been achieved. Therefore, one aspect of the present disclosure provides an efficient and precise method for separating C3-epi-25-OH-Vit-$D_3$ using $CO_2$-based chromatography. The methods described herein comprise, at least in part, a $CO_2$-based chromatography method for separating metabolites of Vitamin D, wherein at least a portion of the $CO_2$ used is in a supercritical state (or near supercritical state or STP).

The present disclosure also provides efficient and precise methods for separating low concentration metabolites (e.g., 1,25-$(OH)_2$-Vit-D or 1,24,25-$(OH)_3$-Vit-D) and derivatives thereof, metabolites involved in the determination of a person's Vitamin D status (25-OH-Vit-$D_2$, 25-OH-Vit-$D_3$, and C3-epi-25-OH-Vit-$D_3$), and enzymes and metabolites involved or implicated in Vitamin D metabolic processes.

In addition to other advantages, the $CO_2$-based chromatography methods described herein minimize consumption of mobile phase solvents (e.g., methanol) thereby generating less waste for disposal and reducing the cost of analysis per sample. Also, because relatively short chromatographic run times (less than 5 minutes) are typically achieved with effective separation, the unique speed and resolution provided by the $CO_2$-based chromatography methods described herein serve as a key element in developing high-throughput routine screening assays.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 1 is an exemplary comparison of A) $CO_2$-based chromatography/MS/MS; and B) UPLC/MS/MS separations of 25-OH-Vit-$D_3$ and C3-epi-25-OH-Vit-$D_3$.

FIG. 2 represents a rapid $CO_2$-based chromatography/MS/MS analysis of Vitamin D metabolites using a BEH C18 column (1.7 um, 2.1 mm×50 mm).

DETAILED DESCRIPTION OF THE INVENTION

Figure 3:
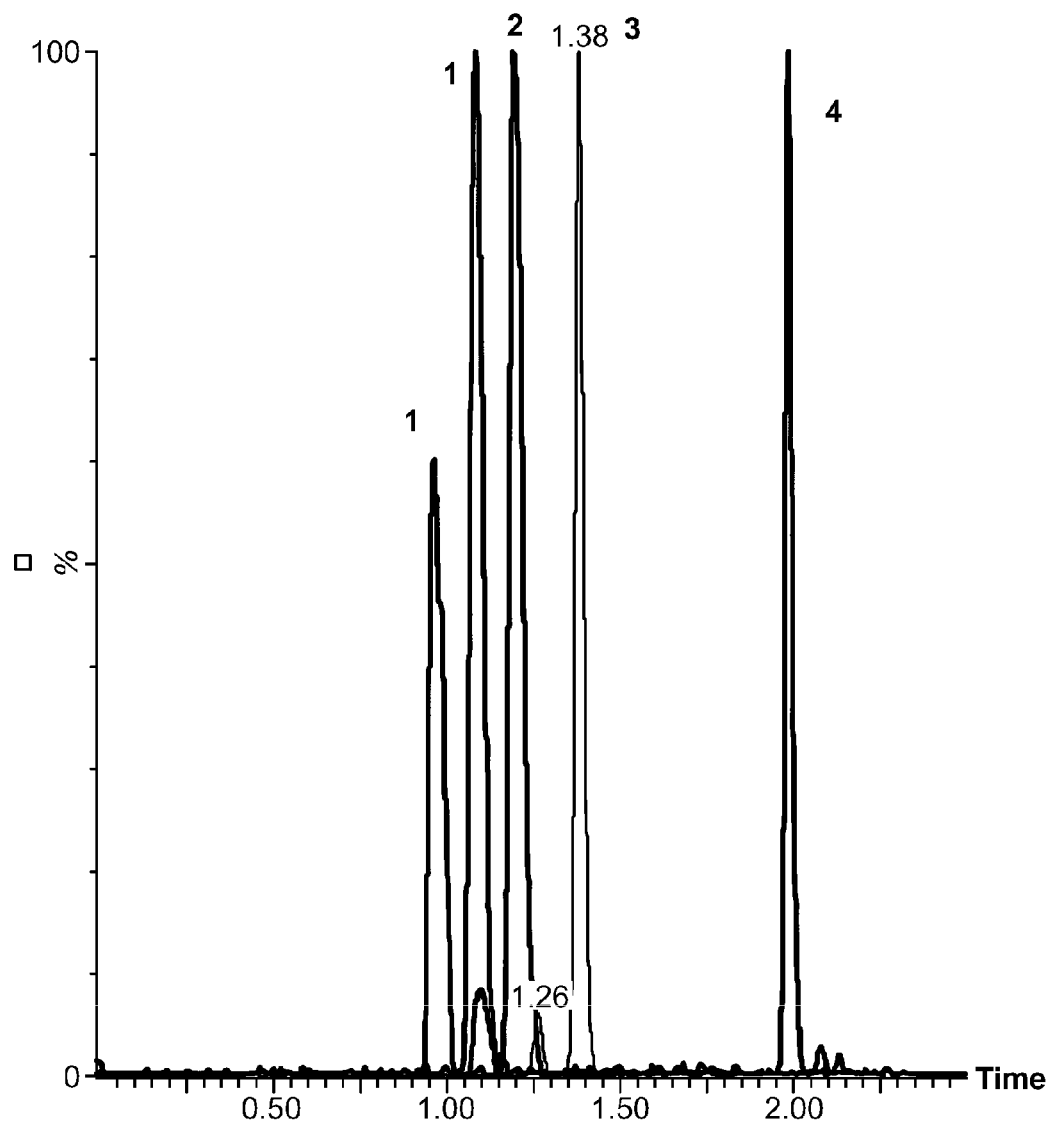
FIG. 3 represents a rapid $CO_2$-based chromatography/MS/MS analysis of Vitamin D metabolites including the C3-epi-25-OH-Vit-$D_3$ using a fluorophenyl based column (1.7 um, 2.1 mm×150 mm).

In one embodiment, the present disclosure provides a method of separating one or more metabolites of Vitamin D, comprising: placing a sample in a $CO_2$-based chromatography system comprising a chromatography column; and eluting the sample by a gradient of organic solvent and a mobile phase fluid comprising $CO_2$ to substantially resolve the one or more metabolites. In some embodiments, the retention times for the one or more metabolites are less than 5 minutes, such as, e.g., from about 0.5 to about 3 minutes.

In one embodiment, the chromatography column comprises particles having an average size of about 1.7, about 3.5, or about 5.0 microns. In another embodiment, the chromatography column comprises charged surface hybrid particles having a particle size of about 1.7 microns or about 3.5 microns.

In one embodiment, the chromatography column is a fluorophenyl based chromatography column.

In one embodiment, the one or more metabolites are selected from 25-OH-Vitamin $D_3$; 25-OH-Vitamin $D_2$; C3-epi-25-OH-Vitamin $D_3$; 24, 25-dihydroxy-Vitamin D; 1α,25-dihydroxy-Vitamin D; 23(R), 25-dihydroxy-Vitamin D; 23(S), 25-dihydroxy-Vitamin D; 25,26-dihydroxy-Vitamin D; 4β,25-dihydroxy-Vitamin D; calcitroic acid; and 1,24,25-trihydroxy-Vitamin-D. In another embodiment, the metabolites are 25-OH-Vitamin $D_3$ or C3-epi-25-OH-Vitamin $D_3$.

In one embodiment, the total elution times for the one or more metabolites is about 2 minutes on a chromatography column having a length of about 150 mm.

In one embodiment, the $CO_2$-based chromatography system comprises an operating system pressure of about 1,000 to about 9,000 psi and a backpressure of about 1,000 to about 9,000 psi.

In one embodiment, the $CO_2$-based chromatography system comprises one or more pumps for delivering a flow of the mobile phase fluid comprising $CO_2$; and an injection valve subsystem in fluidic communication with the one or more pumps and the chromatography column.

As described herein, the injection valve subsystem comprises:
an auxiliary valve comprising:
an auxiliary valve stator, comprising a first plurality of stator ports, in fluidic communication with the one or more pumps and the chromatography column; and
an auxiliary valve rotor comprising a first plurality of grooves;
an inject valve comprising:
an inject valve stator comprising a second plurality of stator ports; and
an inject valve rotor comprising a second plurality of grooves;
a sample loop fluidically connected to the inject valve stator for receiving a sample slug to be introduced into a mobile phase fluid flow; and
fluidic tubing fluidically connecting the auxiliary valve stator and the inject valve stator, wherein the auxiliary valve rotor is rotatable, relative to the auxiliary valve stator, between a plurality of discrete positions to form different fluidic passageways within the auxiliary valve; wherein the inject valve rotor is rotatable, relative to the inject valve stator, between a plurality of discrete positions to form different fluidic passageways within the inject valve, and wherein the respective positions of the auxiliary valve rotor and the inject valve rotor can be coordinated in such a manner as to allow the sample loop and the fluidic tubing to be pressurized to a high system pressure with the mobile phase fluid before they are placed in fluidic communication with the chromatography column.

The methods described herein may, further comprise obtaining a mass spectrometer signal of the one or more metabolites.

In other alternative embodiments, the present disclosure provides a method of separating C3-epi-25-OH-Vitamin $D_3$ from a sample (e.g. Vitamin D or a biological sample from a human specimen), comprising:

placing a sample in a $CO_2$-based chromatography system comprising a fluorophenyl based chromatography column; and eluting the sample by a gradient of organic solvent and a mobile phase fluid comprising $CO_2$ to substantially resolve C3-epi-25-OH-Vitamin $D_3$, wherein the retention time for C3-epi-25-OH-Vitamin $D_3$ is less than 5 minutes and wherein the $CO_2$-based chromatography system is defined as above and optionally coupled to a mass spectrometer.

In one embodiment, the retention time for the C3-epi-25-OH-Vitamin $D_3$ ranges from about 0 to about 3 minutes, such as, e.g., from about 1 to about 2 minutes using the $CO_2$-based chromatography system described above.

In another embodiment, the present disclosure provides a method of separating low concentration Vitamin D metabolites (e.g., 1,25-$(OH)_2$-Vit-D or 1,24,25-$(OH)_3$-Vit-D), or derivatives thereof (e.g., derivatives generated by derivatisation methods such as with Cookson-type reagents), from a sample (e.g. Vitamin D), comprising:

placing a sample in a $CO_2$-based chromatography system comprising a chromatography column (e.g., a fluorophenyl based column); and eluting the sample by a gradient of organic solvent and a mobile phase fluid comprising $CO_2$ to substantially resolve the low concentration metabolites, or derivatives thereof, wherein the retention times for the low concentration metabolites, or derivatives thereof, is less than 5 minutes and wherein the $CO_2$-based chromatography system is defined as above and optionally coupled to a mass spectrometer.

Kits for quantifying one or more metabolites of Vitamin D obtained by the methods of any methods described herein are also provided. In one embodiment, a kit may the comprise a first known quantity of a first calibrator, a second known quantity of a second calibrator, and optionally comprising one or more metabolites of Vitamin D, wherein the first known quantity and the second known quantity are different, and wherein the first calibrator, the second calibrator, and the one or more metabolites are each distinguishable in a single sample by mass spectrometry.

The kits as described herein may also comprise instructions for:

(i) obtaining a mass spectrometer signal comprising a first calibrator signal, a second calibrator signal, and one or more metabolites of Vitamin D from the single sample comprising the first known quantity of the first calibrator, the second known quantity of the second calibrator, and optionally comprising one or more metabolites of Vitamin D; and (ii) quantifying one or more metabolites of Vitamin D in the single sample using the first calibrator signal, the second calibrator signal, and the signal of the one or more metabolites of Vitamin D.

In some embodiments, the first calibrator and the second calibrator are each analogues, derivatives, metabolites, or related compounds of the one or more metabolites of Vitamin D.

Kits may also comprise a third known quantity of a third calibrator and a fourth known quantity of a fourth calibrator, wherein the third known quantity and the fourth known quantity are different, and wherein the first calibrator, the second calibrator, the third calibrator, the fourth calibrator, and the one or more metabolites of Vitamin D are each distinguishable in a single sample by mass spectrometry. These kits may also further comprise instructions for:

(i) obtaining a mass spectrometer signal comprising a third calibrator signal, a fourth calibrator signal, and one or more metabolites of Vitamin D from the single sample comprising the third known quantity of the third calibrator, the fourth known quantity of the fourth calibrator, and optionally comprising one or more metabolites of Vitamin D; and (ii) quantifying one or more metabolites of Vitamin D in the single sample using the third calibrator signal, the fourth calibrator signal, and the signal of the one or more metabolites of Vitamin D.

The kits described herein may further comprise additional calibrators, such as, e.g., from 5 to 10 calibrators including both nonzero and blank calibrators. Instructions for obtaining a mass spectrometer signal and quantifying one or more metabolites of Vitamin D using these additional calibrators is also contemplated. In one exemplary embodiment, the kit contains 6 nonzero calibrators and a single blank calibrator.

In one embodiment, the kits described herein comprise one or more metabolites selected from 25-OH-Vitamin $D_3$; 25-OH-Vitamin $D_2$; C3-epi-25-OH-Vitamin $D_3$; 24, 25-dihydroxy-Vitamin D; 1α,25-dihydroxy-Vitamin D; 23(R), 25-dihydroxy-Vitamin D; 23(S), 25-dihydroxy-Vitamin D; 25,26-dihydroxy-Vitamin D; calcitroic acid,4β,25-dihydroxy-Vitamin D; C3-epi-1-α,25-dihydroxy-Vitamin D3, and 1,24,25-trihydroxy-Vitamin-D. In other embodiments, the metabolites are 25-OH-Vitamin $D_3$ or C3-epi-25-OH-Vitamin $D_3$.

Computer readable mediums are also provided such that a computer readable medium may comprise computer executable instructions adapted to:

separating one or more metabolites of Vitamin D, or derivatives thereof, as described herein (e.g., 25-OH-Vitamin $D_3$, 25-OH-Vitamin $D_2$, C3-epi-25-OH-Vitamin $D_3$, 1,25-$(OH)_2$-Vit-D, or 1,24,25-$(OH)_3$-Vit-D, etc.);

obtaining a mass spectrometer signal comprising a first known quantity of a first calibrator, a second known quantity of a second calibrator, and optionally comprising one or more metabolites of Vitamin D, wherein the first known quantity and the second known quantity are different, and wherein the first calibrator, the second calibrator, and the one or more metabolites are each distinguishable in a single sample by mass spectrometry.

The computer readable medium may further comprise executable instructions adapted to quantifying one or more metabolites of Vitamin D in the single sample using the first calibrator signal, the second calibrator signal, and the signal of the one or more metabolites of Vitamin D.

EXAMPLES

General Conditions for the Analysis of Vitamin D Metabolites

The autosampler (Acquity UPC2® Autosampler, Waters Corporation, Milford, Mass.) settings set forth in the Table 1 below were used in the Vitamin D metabolite analyses. Injection volumes were controlled by a sample list (MassLynx™ Software, Waters Corporation, Milford, Mass.) and recorded separately for each analysis.

TABLE 1

| Parameter | Setting |
| --- | --- |
| Load Ahead | Disabled |
| Injection Mode | Partial Loop With Needle Overfill |
| LoopOffline | Disable |
| Weak Wash Solvent Name | |
| Weak Wash Volume | 600 uL |
| Strong Wash Solvent Name | |
| Strong Wash Volume | 200 uL |

TABLE 1-continued

| Parameter | Setting |
|---|---|
| Target Column Temperature | Off C. |
| Column Temperature Alarm Band | Disabled |
| Target Sample Temperature | 4.0 C. |
| Sample Temperature Alarm Band | Disabled |
| Full Loop Overfill Factor | Automatic |
| Syringe Draw Rate | Automatic |
| Needle Placement | Automatic |
| Pre-Aspirate Air Gap | Automatic |
| Post-Aspirate Air Gap | Automatic |
| Column Temperature Data Channel | No |
| Ambient Temperature Data Channel | No |
| Sample Temperature Data Channel | No |
| Sample Organizer Temperature Data Channel | No |
| Sample Pressure Data Channel | No |
| Switch 1 | No Change |
| Switch 2 | No Change |
| Switch 3 | No Change |
| Switch 4 | No Change |
| Chart Out | Sample Pressure |
| Sample Temp Alarm | Disabled |
| Column Temp Alarm | Disabled |
| Run Events | Yes |
| Needle Overfill Flush | Automatic |

Mass spectrometry data was obtained using a tandem quadrupole mass spectrometer (Xevo® TQD tandem quadrupole, Waters Corporation, Milford, Mass.), which was operated under the conditions set forth in Table 2. Eluent from the $CO_2$-based chromatography system (ACQUITY UPC2®, Waters Corporation, Milford, Mass.) was connected to the electrospray source via a splitter device supplied with a methanol make-up flow that was manually controlled. The make-up flow rate was varied to optimise performance. The optimum flow rate was between 0.1 and 0.8 mL/min

TABLE 2

| Parameter | Setting |
|---|---|
| Ionisation | Electrospray +ve |
| Capillary Voltage (kV) | 2.80 |
| Cone Voltage (V) | 30.00 |
| Extractor Voltage(V) | 3.00 |
| RF Voltage (V) | 0.10 |
| Source Temperature (° C.) | 150 |
| Desolvation Temperature (° C.) | 400 |
| Cone Gas Flow (L/Hr) | 50 |
| Desolvation Gas Flow (L/Hr) | 750 |
| Collision Gas Flow (mL/Min) | 0.15 |
| LM 1 Resolution | 6.02 |
| HM 1 Resolution | 14.58 |
| Ion Energy 1 | 0.26 |
| MS Mode Entrance | 50.00 |
| MS Mode Collision Energy | 20.00 |
| MS Mode Exit | 50.00 |
| MSMS Mode Entrance | 1.00 |
| MSMS Mode Collision Energy | 20.00 |
| MSMS Mode Exit | 0.50 |
| LM 2 Resolution | 11.57 |
| HM 2 Resolution | 14.90 |
| Ion Energy 2 | 1.73 |

The multiple reaction monitoring transitions presented in Table 3 were used to monitor the Vitamin D metabolites.

TABLE 3

| Compound | MRM | Dwell Time (S) | Cone Voltage (V) | Collision Energy (eV) | Delay |
|---|---|---|---|---|---|
| 25-OH-D3* | 383.35 > 257.32 | 0.017 | 30.0 | 15.0 | Auto |
| 25-OH-D2 | 395.35 > 269.32 | 0.017 | 30.0 | 15.0 | Auto |
| 1,25-OH2-D3 | 399.40 > 135.10 | 0.017 | 30.0 | 20.0 | Auto |

*Because 25-OH-Vit-$D_3$ and the C3-epimer have identical chemical composition, this MRM channel detected both analytes.

Example 1: Separation and Analysis of 25-OH-Vitamin $D_3$ and C3-epi-25-OH-Vitamin $D_3$ Pure standards of C3-epi-25-OH-Vitamin $D_3$ and 25-OH-Vitamin $D_3$ were dissolved in hexane and analysed in separate injections (2 uL per injection, approximately 300 pg of each analyte) using a $CO_2$-based chromatography system (e.g., ACQUITY UPC2®, Waters Corporation, Milford, Mass.). The $CO_2$-based chromatography system was fitted with a fluorophenyl based column (ACQUITY UPC²™ CSH Fluoro-Phenyl Column, 130 Å, 1.7 μm, 2.1 mm×150 mm, Waters Corporation, Milford, Mass.) and coupled to a tandem quadrupole mass spectrometer (Xevo® TQD tandem quadrupole, Waters Corporation, Milford, Mass.). The column was eluted at a flow rate of 1.0 mL/min using $CO_2$ mobile phase with a gradient of methanol from 5% to 20% over 1.5 min.

Retention times of approximately 1.2 and 1.4 minutes for 25-OH-Vitamin $D_3$ and C3-epi-25-OH-Vitamin $D_3$ respectively, with baseline resolution, is shown by FIG. 1a where the two separate analyses are overlayed. The total run time of 2 minutes demonstrated substantial resolution at approximately 3 times faster when compared to conventional UPLC/MS/MS technologies. For comparison, FIG. 1b shows a human plasma sample that was spiked with C3-epi-25-OH-Vitamin $D_3$ and subjected to liquid-liquid extraction before analysis using an existing UPLC/MS/MS method. Only partial resolution of the isomers is obtained in a 6 minute analysis.

Example 2: Separation and Analysis of 25-OH-Vitamin $D_3$, 25-OH-Vitamin $D_2$, and 1,25-$(OH)_2$-Vitamin $D_3$ Using a C18 UPLC chromatography column (ACQUITY UPLC® BEH C18 Column, 1.7 um, 2.1 mm×50 mm, Waters Corporation, Milford, Mass.), 25-OH-Vit-$D_2$, 25-OH-Vit-$D_3$, and 1,25-$(OH)_2$Vit-$D_3$ were eluted in less than 1.25 minutes using a $CO_2$-based chromatography system (e.g., ACQUITY UPC2®, Waters Corporation, Milford, Mass.). The column was eluted at a flow rate of 2.0 mL/min using $CO_2$ mobile phase with a gradient of 2.5% to 20% methanol over 1.0 min Chromatographic peak widths of approximately 1.5 seconds at the base were observed and shown in FIG. 2. This chromatograph shows that efficient separation of 25-OH-Vit-$D_2$, 25-OH-Vit-$D_3$, and 1,25-$(OH)_2$Vit-$D_3$ can be achieved using a $CO_2$-based chromatography system fitted with a reverse phase C18 column.

Example 3: Separation and Analysis of 25-OH-Vitamin $D_3$, 25-OH-Vitamin $D_2$, 1,25-$(OH)_2$-Vitamin $D_3$, and C3-epi-25-OH-Vitamin $D_3$ Standards for 25-OH-Vitamin $D_2$, 25-OH-Vitamin $D_3$ and 1,25-$(OH)_2$-Vitamin $D_3$ were combined in hexane and 2 uL (approximately 300 pg of each analyte) was analyzed using a $CO_2$-based chromatography system (e.g., ACQUITY UPC2®, Waters Corporation, Milford, Mass.). The $CO_2$-based chromatography system was fitted with a fluorophenyl based column (ACQUITY UPC$^2$™ CSH Fluoro-Phenyl Column, 130 Å, 1.7 μm, 2.1 mm×150 mm, Waters Corporation, Milford, Mass.). The column was eluted at a flow rate of 1.0 mL/min using $CO_2$ mobile phase with a gradient of methanol from 5% to 20% over 1.5 min. In a separate analysis, 2 uL of a hexane solution of C3-epi-25-OH-Vitamin $D_3$ (approximately 300 pg) was analysed under the same conditions. As shown by FIG. 3, when the chromatograms are overlayed, baseline resolution of 25-OH-Vit-$D_3$ and C3-epi-25OH-Vit-$D_3$, with 25OH-Vit-$D_2$ and 1,25-$(OH)_2$-Vit-D was observed with retention times up to approximately 2 min. It was also noted that additional optimization and the use of other column geometries could further enhance the speed of analysis.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

What is claimed is:

1. A method of separating C3-epi-25-OH-Vit-$D_3$, 25-OH-Vit $D_2$, 25-OH-Vit $D_3$, and 1,25-$(OH)_2$-Vit-D from a sample, comprising:
   placing the sample in a $CO_2$-based chromatography system comprising a flurophenyl based chromatography column; and
   eluting the sample by a gradient of methanol and a mobile phase fluid comprising $CO_2$ to substantially resolve each of C3-epi-25-OH-Vit-$D_3$, 25-OH-Vit $D_2$, 25-OH-Vit $D_3$, and 1,25-$(OH)_2$-Vit-D, and
   wherein the resolved C3-epi-25-OH-Vit-$D_3$, 25-OH-Vit $D_2$, 25-OH-Vit $D_3$, and 1,25-$(OH)_2$-Vit-D elute in under 2 minutes.

2. The method of claim 1, wherein at least one of C3-epi-25-OH-Vit-$D_3$, 25-OH-Vit $D_2$, 25-OH-Vit $D_3$, and 1,25-$(OH)_2$-Vit-D is a PTAD-linked derivative.

3. The method of claim 1, further comprising introducing the eluent containing the C3-epi-25-OH-Vit-$D_3$, 25-OH-Vit $D_2$, 25-OH-Vit $D_3$, and 1,25-$(OH)_2$-Vit-D into a mass spectrometer.

4. The method of claim 3, wherein the mass spectrometer is a tandem quadrupole mass spectrometer.

5. The method of claim 1, wherein the methanol is present at about 5% at the beginning of the gradient, and the gradient is from about 5% to about 20% over between 1 to 1.5 minutes.

6. A kit for quantifying C3-epi-25-OH-Vit-$D_3$, 25-OH-Vit $D_2$, 25-OH-Vit $D_3$, and 1,25-$(OH)_2$-Vit D in a sample comprising:
   a known quantity of a C3-epi-25-OH-Vit-$D_3$, 25-OH-Vit $D_2$, 25-OH-Vit $D_3$, and 1,25-$(OH)_2$-Vit D calibration standard;
   a fluorophenyl based chromatography column having an average particle size of about 1.7 microns, wherein the column dimensions are 2.1 mm by 150 mm; instructions configured for
   separating C3-epi-25-OH-Vit-$D_3$, 25-OH-Vit $D_2$, 25-OH-Vit $D_3$, and 1,25-$(OH)_2$-Vit D from the sample using a $CO_2$-based chromatography system, wherein separation includes a gradient of methanol and wherein the resolved C3-epi-25-OH-Vit-$D_3$, 25-OH-Vit $D_2$, 25-OH-Vit $D_3$, and 1,25-$(OH)_2$-Vit D is configured to be eluted in under 2 minutes;
   obtaining a mass spectrometer signal comprising a C3-epi-25-OH-Vit-$D_3$, 25-OH-Vit $D_2$, 25-OH-Vit $D_3$, and 1,25-$(OH)_2$-Vit D signal from the sample comprising the known quantity of C3-epi-25-OH-Vit-$D_3$, 25-OH-Vit $D_2$, 25-OH-Vit $D_3$, and 1,25-$(OH)_2$-Vit D; and
   quantifying C3-epi-25-OH-Vit-$D_3$, 25-OH-Vit $D_2$, 25-OH-Vit $D_3$, and 1,25-$(OH)_2$-Vit D in the sample using the C3-epi-25-OH-Vit-$D_3$, 25-OH-Vit $D_2$, 25-OH-Vit $D_3$, and 1,25-$(OH)_2$-Vit D signal.

7. The method of claim 1, wherein the fluorophenyl based chromatography column comprises particles having an average size of about 1.7 microns.

8. The method of claim 1, wherein the fluorophenyl based chromatography column dimensions are 2.1 mm by 150 mm.

9. The method of claim 1, wherein the mobile phase flow rate is about 1 mL/min.

10. The method of claim 1, wherein the fluorophenyl based chromatography column comprises particles having an average size of about 1.7 microns, wherein the column dimensions are 2.1 mm by 150 mm, and wherein the mobile phase flow rate is about 1 mL/min.

11. The kit of claim 6, wherein the methanol is present at about 5% at the beginning of the gradient, and the gradient is from about 5% to about 20% over between 1 to 1.5 minutes.

* * * * *